(12) United States Patent
Chen et al.

(10) Patent No.: US 8,715,671 B2
(45) Date of Patent: May 6, 2014

(54) COMPOSITIONS AND METHODS FOR MODULATING IMMUNE RESPONSE

(71) Applicant: Asia Hepato Gene Co., Kaohsiung (TW)

(72) Inventors: David C. P. Chen, Kaohsiung (TW); Yi-Shu Chung, Kaohsiung (TW)

(73) Assignee: Asia Hepato Gene Co., Kaohsiung (TW)

( * ) Notice: Subject to any disclaimer, the term of this patent is extended or adjusted under 35 U.S.C. 154(b) by 18 days.

(21) Appl. No.: 13/727,277

(22) Filed: Dec. 26, 2012

(65) Prior Publication Data

US 2013/0115304 A1    May 9, 2013

Related U.S. Application Data

(62) Division of application No. 12/831,565, filed on Jul. 7, 2010, now abandoned.

(51) Int. Cl.
   *A61K 39/395*   (2006.01)
   *A61K 39/40*    (2006.01)
   *A61K 39/42*    (2006.01)

(52) U.S. Cl.
   USPC ...................................... 424/157.1

(58) Field of Classification Search
   None
   See application file for complete search history.

(56) References Cited

U.S. PATENT DOCUMENTS

2001/0021393 A1* 9/2001 Kodama et al. ............... 424/581
2002/0197259 A1* 12/2002 Kodama et al. ............ 424/157.1

OTHER PUBLICATIONS

Ji-Hyun Shin et al., "Use of Egg Yolk-Derived Immunoglobulin as an Alternative to Antibiotic Treatment for Control of *Helicobacter pylori* Infection," Clinical and Diagnostic Laboratory Immunology, Sep. 2002, vol. 9, No. 5, p. 1061-1066.

\* cited by examiner

*Primary Examiner* — Gary Nickol
*Assistant Examiner* — Khatol Shahnan-Shah
(74) *Attorney, Agent, or Firm* — WPAT, P.C.; Anthony King

(57) ABSTRACT

The present invention relates to a method for modulating immune response in a subject, which comprises administering to the subject an effective amount of a composition comprising a yolk or yolk antibody obtained from an egg of a fowl which has been immunized using *Helicobacter pylori* as an antigen. In particular, the method of the invention is effective in enhancing production of IFN-γ and suppressing production of IL-4 and IL-5 in a subject. Also provided is a composition which comprises said yolk or yolk antibody in combination with polypore and chitosan.

7 Claims, No Drawings

COMPOSITIONS AND METHODS FOR MODULATING IMMUNE RESPONSE

CROSS-REFERENCE TO RELATED APPLICATIONS

This application is a Divisional of the pending U.S. patent application Ser. No. 12/831,565 filed on Jul. 7, 2010, all of which is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded.

Consequently, the Patent Office is asked to review the new set of claims in view of the entire prior art of record and any search that the Office deems appropriate.

FIELD OF THE INVENTION

The present invention relates to the compositions and methods for modulating immune response.

BACKGROUND OF THE INVENTION

The immune system is a defense system for protecting a subject against potentially harmful substances such as microorganisms, toxins, cancer cells, blood or tissues of another subject. The immune system is composed of two major subdivisions, the innate immune system and the acquired immune system. The innate immunity system, also called the non-specific immune system, is the first line of defense, which provides immediate protection; its major components include natural killers, macrophages, neutrophils, eosinophils, etc. The acquired immunity system, also called the specific immune system, acts as the second line of defense, which requires some time to react to a specific antigen; its major components include T cells and B cells.

The acquired immune system comprises two types of immune responses, T-helper-1 (Th1)-type and T-helper-2 (Th2)-type. Th1-type responses provide cell-mediated immunity, involving secretion of interleukin-2 (IL-2) and interferon-r (IFN-r), and activation of cytotoxic lymphocytes (CTLs), which can provide protection against viral infection and cancer cells. Th2-type responses provide humoral immunity, involving secretion of interleukin-4 (IL-4) and interleukin-5 (IL-5) and activation of B cells, which can provide protection against free bacteria or parasites. However, over secretion of IL-4 and IL-5 is related to allergy and inflammation.

Immunity can result from either passive or active immunization. Active immunization produce immunity against a certain foreign substance (e.g. a pathogen) after the body is exposed to it and thus activated to produce such immunity. On the other hand, passive immunization involves transfer of immune components (typically antibodies) against a particular pathogen from one individual to another; the body per se however does not actively produce the immunity. In general, active immunization requires relatively longer time to produce the immunity which is lasting while passive immunity provides faster immunity which is not lasting.

U.S. Pat. No. 6,464,982 describes an immune system stimulator comprising a variety of herbals, which results in secretion of IL-1 without causing an increase in production of IL-4.

Pathogen specific antibodies can be isolated from egg-yolk of hens which have been immunized with the pathogen as an antigen for use in passive immunotherapy for treatment of certain diseases caused by the pathogen. This technique has been developed for many years and isolation of antibodies to common pathogens causing diarrhea, such as *Salmonella Bacillus* (American Journal of Veterinary Research 59:416-20) and the Annular virus (Journal of Infectious Diseases 142:439-41 and Archives of Virology 138:143-8), using this technique have been reported. The period of diarrhea can be reduced after administration of such antibodies to patients in need. Shin et al. reported that antibodies specific to *Helicobacter pylori* can be isolated from egg yolk of hens immunized with *H. pylori* and described that such isolated antibodies can be used for treatment of infectious diseases caused by *H. pylori* (Clinical and Diagnostic Laboratory Immunology, 9(5): 1061-1066). Marquardt et al. (U.S. Pat. No. 7,355,092) disclosed genetic vaccines against *E. coli* fimbrial antigens and a method for isolating antibodies from chicken egg yolk for passive immunization of animals to control diarrhoeal diseases using the genetic vaccines.

BRIEF SUMMARY OF THE INVENTION

The present invention is based on the unexpected finding that a composition comprising a yolk or yolk antibody obtained from an egg of a fowl which has been immunized using *Helicobacter pylori* as an antigen can modulate immune response in a subject.

Accordingly, the present invention provides a method for modulating immune response in a subject comprising administering to the subject an effective amount of a composition comprising a yolk or yolk antibody obtained from an egg of a fowl which has been immunized using *Helicobacter pylori* as an antigen. In particularly, the method of the invention can promote production of IFN-γ□ and suppress production of IL-4 and IL-5 in a subject.

Also provided is a composition for modulating immune response in a subject which comprises a yolk or yolk antibody obtained from an egg of a fowl which has been immunized using *Helicobacter pylori* as an antigen, in combination with polypore and chitosan. In one embodiment, the yolk or yolk antibody, polypore and chitosan are present in a ratio of about 2:2:1 by weight in the composition of the invention.

The various embodiments of the present invention are described in details below. Other characteristics of the present invention will be clearly presented by the following detailed description about the various embodiments and claims.

It is believed that a person of ordinary knowledge in the art where the present invention belongs can utilize the present invention to its broadest scope based on the description herein with no need of further illustration. Therefore, the following description should be understood as of demonstrative purpose instead of limitative in any way to the scope of the present invention.

DETAILED DESCRIPTION OF THE INVENTION

Unless defined otherwise, all technical and scientific terms used herein have the meaning commonly understood by a person skilled in the art to which this invention belongs.

The articles "a" and "an" are used herein to refer to one or more than one (i.e., at least one) of the grammatical object of the article.

Described herein is a method for modulating immune response in a subject which comprises administering to the subject an effective amount of a composition comprising a yolk or yolk antibody obtained from an egg of a fowl which has been immunized using *Helicobacter pylori* as an antigen.

The term "modulating immune response" or "modulation of immune response" as used herein with respect to an agent or substance means that the agent or substance is capable of changing or modifying at least one function of the immune system of a subject after being introduced into the subject, including but are not limited to, changing or modifying the number, amount or activity level of components or effector cells (e.g. cytokines, antibodies or natural killer cells) of the subject's immune system. Standard assays for determining such capacity of an agent or substance are known in the art such as those published by Department of Health, Executive Yuan, R.O.C. (TAIWAN) including "Cytokine Secretion Assays" and "Natural Killer Cell Cytotoxicity Assays." Specifically, statistically significant increase or decrease of the number, amount or activity level of components or effector cells of the immune system as measured by the standard assays is considered "modulating immune response" or "modulation of immune response." An "effective amount" refers to the amount of a composition or agent effective to achieve the above-described modulation of immune response.

The term "subject" as used herein includes human and non-human animals such as companion animals (e.g., dogs, cats, and the like), farm animals (e.g., cows, sheep, pigs, horses, and the like) or laboratory animals (e.g., rats, mice, guinea pigs, and the like).

The term "immunization" as used herein refers to a process known in the art for inducing an immune response in an animal by introducing an antigenic agent or substance into the animal (e.g., by injection, by mucosal challenge, etc.), which preferably results in a specific immune response to the antigenic agent or substance. The antigenic agent or substance can be introduced to the animal, with or without the use of adjuvants.

It is expectedly found herein for the first time that a composition comprising a yolk or yolk antibody obtained from an egg of a fowl which has been immunized using *Helicobacter pylori* as an antigen has capacity of modulating immune response in a subject. As shown in the examples below, animals fed with such composition exhibited enhanced Th1 immune responses (increased secretion of IFN-γ) and suppressed Th2 immune response (decreased secretion of IL-4), indicating that the composition of the invention has potential to enhance the immunity against foreign pathogens (Th1 immune response) without inducing undesired inflammation (Th2 immune response).

*H. pylori* as used herein can be obtained from a commercial source, such as the American Type Culture Collection (ATCC), which can be the whole bacteria or its antigenic fragment or any combinations thereof. Specifically, the bacteria are cultured for a sufficient period of time, and then harvested, lysed (e.g. by sonication) and centrifuged to obtain a *H. pylori* cell lysate (supernatant). The cell lysate can be mixed with a proper adjuvant as suggested in this art (e.g. a complete Freund adjuvant) and then administered to a fowl via muscle injection, for example, for immunization. Further immunization of a *H. pylori* cell lysate with an incomplete Freund adjuvant, for example, is preferred to boost the immune response in the fowl. In general, one to three times of boost or more is suggested, and the period of time between each immunization is about 7 to 21 days, preferably about 14 days. After the immunization, eggs laid by the fowl are collected and the yolk is isolated from the eggs. Optionally, the yolk is further processed as needed e.g. lyophilized for the purpose of easy storage and subsequent filling in capsules, for example. The presence and title level of specific antibodies in the yolk can be confirmed by any method such as an immunological assay known in art e.g. Enzyme-linked immunosorbent assay (ELISA) or a method using agglutination reaction.

The techniques of immunizing a fowl, harvesting eggs and collecting yolk are well known in the art, such as those described in Shih et al. Examples of fowls as used herein include but are not limited to chickens, ducks, and geese. Certain steps and details of the procedures are described in the examples as below.

In one embodiment, the composition of the invention further contains polypore and chitosan, in addition to a yolk or yolk antibody obtained from an egg of a fowl which has been immunized using *H. pylori* as an antigen as above-described.

Polypore (*Phellinus baumii*) is a hard, brittle mushroom with pores underneath its cap, which has been used as Chinese medicine for many years. Polypore has been reported to have antioxidant, anti-mutant and anticancer activities and effects of liver protection. Polypore is commercially available.

Chitosan is a product by complete or partial deacetylation of chitin, which may be produced from crustaceans such as crabs or shrimp or fungi. Chitosan is of a general formula as below:

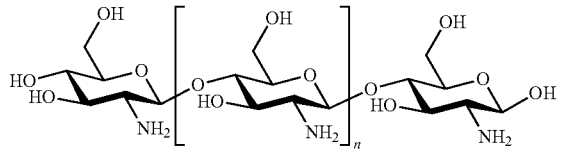

The degree of deacetylation (% DD) can be determined by NMR spectroscopy and the % DD in commercial chitosans is in a range of about 60% to 100%.

In a certain example, the composition of the invention comprises a yolk or yolk antibody obtained from an egg of a fowl immunized with *Helicobacter pylori* as above-described, in combination with polypore and chitosan, particularly in ratio of about 2:2:1 by weight.

For delivery purpose, the composition of the invention is preferably formulated with an acceptable carrier according to the disclosure herein and established methods in the art. "Acceptable" means that the carrier must be compatible with the active ingredient (s) contained in the composition, preferably capable of stabilizing the active ingredient (s), and not deleterious or mildly deleterious to the subject to be treated. The carrier may serve as a filler, binder, wetting agent, lubricant, or antioxidant. Examples of fillers include but are not limited to starches, lactose, sucrose, glucose, mannitol, and silicic acid. Examples of binders include but are not limited to carboxymethylcellulose, alginates, gelatin, polyvinylpyrrolidinone, sucrose, and acacia. Examples of wetting agents include but are not limited to cetyl alcohol and glycerol monostearate. Examples of lubricants include but are not limited to talc, calcium stearate, magnesium stearate, solid polyethylene glycols, and sodium lauryl sulfate. Examples of antioxidants include but are not limited to α-tocopherol, butylhydroxyanisole, butyl hydroxytoluene, ascorbic acid and the like. The composition of the invention may contain other inactive ingredients such as stabilizers, coloring agents, and/or preservatives.

The composition of the invention can be formulated in any forms as desired using conventional techniques in view of the teachings provided in the specification. In a certain example, the composition of the invention is in the form of powder, more specifically are lyophilized powders, which may be further loaded into capsules. In other examples, the composition of the invention is in the form of tablets, pills, particles, lozenges, sachets, cachets, elixirs, suspensions, emulsions, solutions, syrups, soft and hard gelatin capsules, suppositories, or sterile injectable solutions.

The pharmaceutical composition of the invention may be delivered through any medically acceptable route such as orally, parentally (e.g. intramuscularly, intravenously, subcutaneously, interperitoneally), topically, transdermally, by inhalation and the like. In one embodiment, the composition is orally administered to a subject in need.

The composition of the invention can modulate the immune response in a subject, particularly enhance cytotoxicity activity of natural killer cells, increase IFN-γ production, and suppress IL-4 or IL-5 production. It is suggested that the composition of the invention is helpful for strengthening the immunity against foreign pathogens without inducing undesired inflammation or allergies. It is also suggested that the composition of the invention can be used for general health care in a normal subject or for special care in a subject whose immune system is suppressed or depressed such as a mammal suffering from tumor, AIDS, chronic infections, and disease showing a low activity level of natural killer cells or a decreased amount of IFN-γ.

The composition of the invention can be formulated as a medicament or food additive which can be added to food or snacks e.g. candy or milk.

The dose of the composition of the present invention may vary with factors such as the route of administration, the size and species of the subject to receive the agent, and the purpose of the administration. The dose in each individual case may be determined empirically by a skilled artisan according to the disclosure herein and established methods in the art.

The present invention will now be described more specifically with reference to the following embodiments, which are provided for the purpose of demonstration rather than limitation.

Materials

Ovalbumin (Ova), heparin, Concanavalin A (ConA), lipopolysaccharide (LPS), 3-(4,5-dimethylthiazol-2-yl)-2,5-diphenyl tetrazolium bromide (MTT), dimethyl sulfoxid (DMSO), Freund's adjuvants, Hank's balanced salts solution (HBSS), Delbecco's modified Eagle's medium (DMEM), RPMI 1640, trypan blue, Tween-20, and bovine serum albumin (BSA) were purchased from Sigma-Aldrich. Fetal bovine serum (FBS) was purchased from PAA Laboratories GmbH (Pasching, Austria).

Antibodies including α-H2Kd FITC, α-1-Ad FITC, α-NK FITC, α-CD3 FITC, α-CD19 PE, α-CD4 FITC, and α-CD8 PE were purchased from PharMingen International.

DuoSet ELISA Development System was purchased from R&D SYSTEMS (Minneapolis, Minn., U.S.A.). Phagotest kit was purchased from ORPEGEN Pharma (Heidelberg, Germany), including opsonized FITC-labelled *E. coli*, quenching solution, DNA staining solution, lysis solution and washing solution. LIVE/DEAD Cell-Mediated Cytotoxicity Kit was purchased from Molecular Probe (Eugene, Oreg., U.S.A.) including DIOC18 (3,3'-dioctadecyloxacarbocyamine) and propidium iodide. Mouse Ig ELISA Quantitation Kit was purchased from Bethyl (Montgomery, Tex., U.S.A.).

Tetramethylbenzidine (TMB) solution was purchased from Kirkegaard & Perry Laboratories (Gaithersburg, Md., U.S.A.).

$NH_4Cl$, $KHCO_3$, $Na_2$-EDTA, NaCl, KCl, $Na_2HPO_4$, $KH_2PO_4$, $H_3PO_4$, sucrose, sodium carbonate, and Tris are reagent-grade chemicals.

EXAMPLE 1

Preparation of a *H. pylori* Cell Lysate

A *H. pylori* cell lysate was prepared following the method as described in Shin et al (supra). Briefly, *H. pyloris* obtained from the American Type Culture Collection (ATCC 43504) was cultured in the brucella broth (Difco laboratory, Detroit, Mich., US) including 5% fetal calf serum and antibiotics including 2.5 amphotericin B, 10 μg/ml vancomycin, 5 μg/ml trimethoprin, and 2.5 IU/ml polymyxin B (American Sigma Chemistry Company) at 37° C., 10% $CO_2$ with shaking at the speed of 200 rpm. Then, the culture was centrifuged at 12,000×g for 10 min, sonicated, and centrifuged. The supernatant was collected to obtain a *H. pylori* cell lysate. The protein concentration of the lysate was measured with the bicinchoninic acid method (Pierce, Rockford, III).

EXAMPLE 2

Immunization of Hens and Preparation of Yolk Lyophilized Powders

The above-described *H. Pylori* lysate obtained in Example 1 (protein concentration, 200 μg/ml) was mixed with the same volume of a complete Freund adjuvant (Difco laboratory, Detroit, Mich., US). The mixture was intramuscularly injected to hens (25 week age, Brown Leghorn hens, n=15). Each hen had 4 positions at the leg muscle to accept the injection; the dosage for each position is 250 μl. After the first injection, a mixture of the *H. Pylori* lysate and the same volume of an incomplete Freund adjuvant was intramuscularly injected to the hens every other week for three times to boost the immune response. After one month following the last boost, the eggs laid by the hens were collected and the yolk was removed and lyophilized to obtain yolk lyophilized powders, called "IgY-HP." IgY-HP was confirmed to have an adequate title of antibodies for quality control.

EXAMPLE 3

Animal Experiments 3.1 Animals

Female BALB/c mice, 6-week old, were used in the following experiments. They were purchased from BioLASCO Taiwan Co., Ltd. (Taipei, Taiwan), and maintained in accordance with the procedures approved by the Food Industry Development Research institute (Hsinchu, Taipei). Briefly, mice after purchased were observed for two weeks and those with abnormal behaviors (fearing light, dehydration, etc.) or having weights out of the average weight±2 standard deviation were discarded. Each of the cages was placed with a layer of sawdust (the American NEPCO Corporation, Warrensburg, N.Y.), which was sterilized before placement and replaced twice times per week. The feed was PMI 5001 specific for experimental mice purchased from Purina (USA). The mice were kept at 23±2° C., 50±10% relative humidity, and 12:12 (hours) light dark cycle.

3.2 Feeding

The mice were randomly divided into two groups, the IgY-HP experimental group and the water control group. There were 12 mice in each group. For the IgY-HP experimental group, each of the mice was fed with a IgY-HP suspension, prepared by mixing 5.119 mg IgY-HP in 0.2 ml deionized water, through a stomach tube every day for ten weeks (from 6-week old to 16-week old). For the water control group, each of the mice was fed with the same volume of deionized water every day.

3.3 Immunization

The mice during the above-described feeding procedure were immunized with Ova. First, blood samples were collected from the tails of the mice (6-week old) before the feeding procedure started. The mice were then immunized three times at 7-week, 10-week and 13-week old, respectively. The first immunization was conducted by subcutaneous injection of 2 μg ova antigen mixed with a complete Freund adjuvant (100 μl). The second and third immunizations were respectively conducted by subcutaneous injection of 10 μg ova antigen mixed with an incomplete Freund adjuvant (100 μl). Blood samples were collected regularly from the tails of the mice after each immunization.

The mice were sacrificed by $CO_2$ suffocation when they were at 16-week old after the last feeding. Blood samples (0.7 to 1.0 ml) were collected from the heart of the mice, and stored at 4° C. The bodies of the mice were sprayed with alcohol for disinfection and then moved to a clean bench for subsequent operation. Table 1 shows the procedure of feeding and immunizations to the mice as above described.

TABLE 1

Procedures of feeding and immunizations

| Run Time (week) | mouse age (week) | Events |
| --- | --- | --- |
|  |  | Purchasing, adapting to the environment |
| 0 | 6 | Weighting, grouping, blood sampling, starting feeding |
| 1 | 7 | First Immunization |
| 2 | 8 |  |
| 3 | 9 | Blood sampling |
| 4 | 10 | First Immunization |
| 5 | 11 |  |
| 6 | 12 | Blood sampling |
| 7 | 13 | First Immunization |
| 8 | 14 |  |
| 9 | 15 |  |
| 10 | 16 | Blood sampling, mice scarified. |

EXAMPLE 4

Analysis of the Body Weight of Mice

During the 10-week period of feeding (from 6-week old to 16-week old), each of the mice were weighed and observed for growth condition. Table 2 shows the results.

TABLE 2

Measurement results of mice body weight.

| Run time (week) | Mouse age (week) | Water control group (n = 12) | IgY-HP experiment group (n = 12) |
| --- | --- | --- | --- |
| 0 | 6 | 20.9 ± 1.0 | 20.9 ± 0.7 |
| 1 | 7 | 21.3 ± 0.7 | 21.4 ± 0.3 |
| 2 | 8 | 19.6 ± 0.6 | 19.8 ± 0.6 |
| 3 | 9 | 21.2 ± 1.0 | 21.3 ± 0.7 |
| 4 | 10 | 22.2 ± 0.9 | 22.2 ± 0.6 |
| 5 | 11 | 23.4 ± 0.7 | 23.1 ± 0.7 |
| 6 | 12 | 24.7 ± 0.8 | 23.7 ± 0.6* |
| 7 | 13 | 25.1 ± 0.8 | 24.1 ± 0.6* |

TABLE 2-continued

Measurement results of mice body weight.

| Run time (week) | Mouse age (week) | Water control group (n = 12) | IgY-HP experiment group (n = 12) |
| --- | --- | --- | --- |
| 8 | 14 | 25.2 ± 0.7 | 24.8 ± 0.7* |
| 9 | 15 | 25.8 ± 1.2 | 25.1 ± 0.6 |
| 10 | 16 | 25.9 ± 1.1 | 25.3 ± 0.6 |

The results were expressed by the mean value ± standard deviation (mean ± SD). The body weight unit is the gram (gm).
The symbol "*" means a significant difference between the experiment group and the water control group ($p < 0.05$).

As shown in Table 2, during the period from $6^{th}$ to $8^{th}$ week, the body weight of the mice of the IgY-HP experimental group appears to be lower than that of the water control group. However, when the mice grew older ($9^{th}$ to $10^{th}$ week), the body weight of the mice restored without differences between the IgY-HP experimental group and the water control group. It implies that the decrease of the body weight of the mice of the IgY-HP experimental group is temporary and irrelevant to the ingredients fed to the mice.

EXAMPLE 5

Analysis of the Total Amount of Non-Specific IgG Antibodies

Blood samples collected from the sacrificed mice after the above-described 10-week feeding procedure were analyzed for the total amount of the IgG antibodies by Mouse Ig ELISA Quantitation Kit (Bethyl Corporation, Montgomery, Tex., US). Table 3 shows the results.

TABLE 3

The total amount of the non-specific IgG antibodies

| Total amount of IgG (μg/mL) | Water control group (n = 12) | IgY-HP experiment group (n = 12) |
| --- | --- | --- |
| Before immunization | 57 ± 12 | 51 ± 8 |
| First immunization | 120 ± 14 | 133 ± 26 |
| Second immunization | 344 ± 99 | 533 ± 173* |
| Third immunization | 830 ± 246 | 1010 ± 317 |

The results were expressed by the mean value ± standard deviation (mean ± SD).
The symbol "*" means a significant difference between the experiment group and the water control group ($p < 0.05$).

As shown in Table 3, the total amount of non-specific IgG antibodies in the IgY-Hp experimental group is higher than that in the water control group, implying that feeding IgY-HP enhances the total amount of non-specific IgG antibodies in the blood of the mice after immunization.

EXAMPLE 6

Analysis of the Cytotoxicity Activity of Non-Specific Natural Killer Cells

The spleens were removed from the sacrificed mice after the above-described 10-week feeding procedure and placed in 5 ml culture medium. The spleens were suppressed and grinded gently using the even end of the syringe propeller until the color of the spleens turned to white, indicating that the spleen cells were drifted away from the connective tissue and released into the culture medium. Then, the culture medium containing the spleen cells was transferred to centrifuge tubes and settled for 5 to 10 minutes to allow the connective tissues or large debris to be precipitated to the underneath of the tube. The supernatant was collected and removed to another centrifuge tube and then centrifuged at 250×g for 5 minutes. The supernatant was discarded and the pellets were re-suspended by gently patting the tube. 5 ml of ice-cold ACK red blood cell lysis buffer was added to the tube and mixed with the cells inside. After centrifugation at 250×g for 5 minutes, the supernatant was discarded and the cell pellet was washed by 10 ml HBSS buffer twice. The cells were re-suspended in 10 ml culture medium and the cell density was measured using the trypan blue staining method.

The cytotoxicity activity of natural killer cells was measured using LIVE/DEAD cell-mediated cytotoxicity kit (American Member Probe Company, Eugene, US). Briefly, Yac-1 cells, the target cells of natural killer cells, were labeled by the dye, DIOC18 at 37° C., 5% $CO_2$ for 16 hours, and then the spleen cells were mixed with the labeled target cells in a ratio of 1:100 or 1:200 and incubated at 37° C., 5% $CO_2$ for 4 hours. The negative control was conducted according to the same procedure except that RPMI 1640 medium (10% fetal calf blood serum), in place of the spleen cells, was mixed with the labeled target cells. The cell numbers were measured by flow cytometry.

The cytotoxicity activity (%) of natural killer cells was calculated according to the formula "the mortality rate (%) of the target cells in the experimental group–the mortality rate (%) of the target cells in the negative control group." Table 4 shows the results.

TABLE 4

The cytotoxicity activity (%) of natural killer cells

| Cytotoxicity activity of the natural killer cells (%) | Water control group (n = 10) | IgY-HP experiment group (n = 10) |
|---|---|---|
| E/T = 100:1 | 35.2 ± 3.4 | 39.0 ± 5.0 |
| E/T = 200:1 | 39.9 ± 3.1 | 45.8 ± 5.3* |

The results were expressed by the mean value ± standard deviation (mean ± SD).
The symbol "*" means a significant difference between the experiment group and the water control group ($p < 0.05$).

As shown in Table 4, the cytotoxicity activity of natural killer cells in the IgY-HP experimental group is significantly higher than that in the water control group, indicating that IgY-HP is effective in enhancing the cytotoxicity activity of natural killer cells.

EXAMPLE 7

Analysis of Production of Non-Specific Cytokines

In a 24 well culture plate, culture medium (control group), or ConA at a final concentration of 5 µg/ml or LPS at a final concentration of 10 µg/ml in culture medium was respectively added to each well. The spleen cell suspension obtained in Example 4 was added to the wells (0.4×10⁶ cells/well), and incubated at 37☐, 5% $CO^2$ for 24 and 48 hours. The supernatant was then collected and analyzed for the amount of non-specific cytokines, IL-2, IFN-r, IL-4 and IL-5, in the supernatant by a sandwich enzyme-linked immunosorbent assay (sandwich-ELISA) using DuoSet ELISA Development System (American R & The D system company, Minneapolis, Minn., USA). Table 5 shows the results.

TABLE 5

Results of production of non-specific cytokine secretion

| | Water control group (n = 10) | IgY-HP experiment group (n = 10) |
|---|---|---|
| IL-2 (pg/mL) | | |
| culture medium | 17 ± 99 | 13 ± 7 |
| Con A | 9423 ± 2463 | 10225 ± 2099 |
| LPS | 19 ± 6 | 18 ± 3 |
| IFN-γ (pg/mL) | | |
| culture medium | 0 ± 0 | 0.37 ± 1.18 |
| Con A | 3013 ± 814 | 3549 ± 1213 |
| LPS | 960 ± 529 | 1513 ± 658 |
| IL-4 (pg/mL) | | |
| culture medium | 0 ± 0 | 0 ± 1 |
| Con A | 337 ± 189 | 349 ± 153 |
| LPS | 12 ± 2 | 9 ± 2* |
| IL-5 (pg/mL) | | |
| culture medium | 0 ± 0 | 0 ± 0 |
| ConA | 470 ± 272 | 260 ± 93* |
| LPS | 25 ± 5 | 26 ± 7 |

The results were expressed by the mean value ± standard deviation (mean ± SD).
The symbol "*" means a significant difference between the experiment group and the water control group ($p < 0.05$).

As shown in Table 5, the production of Th2 cytokines, IL-4 and IL-5, in the IgY-HP experimental group is significantly lower than that in the water control group ($p<0.05$), indicating that IgY-HP has potential to inhibit Th2 immune response.

EXAMPLE 8

Analysis of Production of Specific Cytokines

Analysis of production of specific cytokines was conducted based on the procedure as in Example 7. Briefly, in a 24 well culture plate, culture medium (control group) or Ova A at a final concentration of 100 µg/ml in culture medium was respectively added to each well. The spleen cell suspension obtained from Example 4 was added to the wells (0.4×10⁶ cells/well), and incubated at 37° C., 5% $CO^2$ for 24 and 48 hours. The supernatant was then collected, and analyzed for the amount of ova-specific cytokines, IL-2, IFN-r, IL-4 and IL-5, in the supernatant by a sandwich enzyme-linked immunosorbent assay (sandwich-ELISA) using DuoSet ELISA Development System (American R & The D system company, Minneapolis, Minn., USA). Table 6 shows the results.

TABLE 6

Results of production of specific cytokines

| | Water control group (n = 10) | IgY-HP experiment group (n = 10) |
|---|---|---|
| IL-2 (pg/mL) | 50 ± 12 | 56 ± 21 |
| IFN-γ (pg/mL) | 535 ± 190 | 751 ± 191* |
| IL-4 (pg/mL) | 19 ± 6 | 9 ± 3* |
| IL-5 (pg/mL) | 169 ± 86 | 27 ± 11* |

The results were expressed by the mean value ± standard deviation (mean ± SD).
The symbol "*" means a significant difference between the experiment group and the water control group ($p < 0.05$).

As shown in Table 6, the amounts of ova-specific IL-4 and IL-5 (Th2 cytokines) in the IgY-HP experimental group are significantly lower than those in the water control group while the amount of IFN-γ (Th1 cytokine) is significantly higher than those in the water control group, indicating that IgY-HP has potential to promote production of specific Th1 cytokines and lower the production of specific Th2 cytokines.

EXAMPLE 9

IgY-HP Combination Powder

Powders of polypore and chitosan were purchased from the China Biotechnology Company (Taipei, Taiwan), and mixed with the IgY-HP powder obtained in Example 2 in a ratio of 40% (IgY-HP), 40% (polypore) and 20% (chitosan) (w/w). The combined powders were loaded in capsules (0.48 g per capsule).

The mice were fed according to the procedures as described in Example 3. Briefly, the mice were randomly divided into two groups, the experimental group receiving the IgY-HP combination powder and the control group receiving water. There were 8 to 12 mice in each group. For a 70 kg adult, the suggested dosage for general health care is two capsules per day (0.48 g/capsule), and accordingly for a 20 g mouse, the dosage is approximately 2.457 mg per day. For the experimental group, each of the mice was fed with a suspension of IgY-HP combination powder, prepared by mixing approximately 2.457 mg of the above-described IgY-HP combination powder with 0.2 ml deionized water, through a stomach tube every day for ten weeks (from 6-week old to 16-week old). For the control group, each of the mice was fed with the same volume of deionized water every day. The mice during the above-described feeding procedure were immunized with Ova as described in Example 3.

Analysis of production of ova specific cytokines was conducted based on the procedure as described in Example 8. The increase or decrease of the production of cytokines (%) in the experimental group when compared with the control group was calculated according to the formula "(the difference between the amount of the cytokine as measured in the experimental group and that in the control group/the amount of the cytokine as measured in the control group)×100%." Table 7 shows the results.

TABLE 7

Results of production of specific cytokines

| | Increase or decrease of production of specific cytokines (compared to the control group) IgY-HP combination powder |
|---|---|
| IL-2 (pg/mL) | 12% (increase) |
| IFN-γ (pg/mL) | 40% (increase)* |
| IL-4 (pg/mL) | 68% (decrease)* |
| IL-5 (pg/mL) | 59% (decrease)* |

The symbol "*" means a significant difference between the experiment group and the water control group (p < 0.05).

Further, the effects of individual polypore and chitosan on the cytokine production were separately determined. Table 8 shows the results.

TABLE 8

Results of polypore and chitosan on cytokine production

| | Increase or decrease of production of specific cytokines (compared to the control group) | |
|---|---|---|
| | polypore | chitosan |
| IL-2 (pg/mL) | 5% (increase) | ND |
| IFN-γ (pg/mL) | 38% (increase)* | ND |
| IL-4 (pg/mL) | 10% (decrease) | 12% |
| IL-5 (pg/mL) | ND | 23% (decrease) |

ND expressed that has not done on the test.
The symbol "*" means a significant difference between the experiment group and the water control group (p < 0.05).

As shown in Tables 7 and 8, the IgY-HP combination powder significantly reduced production of ova-specific IL-4 and IL-5 and promoted production of ova-specific IFN-γ (p<0.05), indicating the IgY-HP combination powder has potential to promote production of specific Th1 cytokines and lower the production of specific Th2 cytokines, which is superior to the effects of polypore or chitosan alone.

In conclusion, the composition of the invention has the ability to promote the cytotoxicity activity of natural killer cells, to promote production of IFN-γ, and to suppress production of IL-4 and IL-5, and when combined with polypore and chitosan, the effects of such composition of the invention are superior to those of individual polypore or chitosan. The composition of the invention can promote Th1 immune response (IFN-γ) but suppress Th2 immune response (IL-4 and IL-5), which is very helpful for protecting a subject against foreign pathogens without undesired inflammation and allergic responses.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. A method for enhancing production of IFN-γ in a subject in need thereof, comprising administering to the subject a composition comprising, as an active ingredient, a yolk obtained from an egg of a fowl which has been immunized using *Helicobacter pylori* as an antigen, in an amount effective to enhance production of IFN-γ in the subject wherein a sample is collected from said subject and the amount of IFN-γ is measured.

2. The method of claim 1, wherein the fowl is selected from the group consisting of chickens, ducks and geese.

3. The method of claim 1, wherein the fowl is a hen.

4. The method of claim 1, wherein the composition is in the form of powder.

5. The method of claim 1, wherein the composition is orally administered to the subject.

6. The method of claim 1, wherein the composition further comprises polypore and chitosan.

7. The method of claim 6, wherein the yolk, polypore and chitosan are present in a ratio of 2:2:1 by weight in the composition.

* * * * *